US012622616B2

(12) United States Patent
Burkholz

(10) Patent No.: US 12,622,616 B2
(45) Date of Patent: May 12, 2026

(54) VASCULAR ACCESS DEVICE BLOOD DRAW SYSTEM WITH SEPTUM ACCESS

(71) Applicant: Becton, Dickinson and Company, Franklin Lakes, NJ (US)

(72) Inventor: Jonathan Karl Burkholz, Salt Lake City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 546 days.

(21) Appl. No.: 18/099,556

(22) Filed: Jan. 20, 2023

(65) Prior Publication Data

US 2023/0233119 A1     Jul. 27, 2023

Related U.S. Application Data

(60) Provisional application No. 63/301,749, filed on Jan. 21, 2022.

(51) Int. Cl.
A61B 5/00     (2006.01)
A61B 5/15     (2006.01)

(52) U.S. Cl.
CPC .... A61B 5/150992 (2013.01); A61B 5/15003 (2013.01)

(58) Field of Classification Search
CPC .......... A61B 5/150992; A61B 5/15003; A61B 5/155; A61B 5/150213; A61B 5/150221; A61B 5/150732; A61B 5/15074; A61B 5/153; A61B 5/154; A61M 5/14; A61M 5/158; A61M 25/02
See application file for complete search history.

(56) References Cited

U.S. PATENT DOCUMENTS

| | | | | |
|---|---|---|---|---|
| 9,855,386 B2 * | 1/2018 | Close | ..................... | A61B 5/155 |
| 11,389,624 B2 * | 7/2022 | Cook | ................. | A61B 5/15003 |
| 11,931,531 B2 * | 3/2024 | Scherich | ......... | A61M 25/09041 |
| 12,048,826 B2 * | 7/2024 | Scherich | ............. | A61M 25/007 |
| 12,114,976 B2 * | 10/2024 | Ma | ....................... | A61M 25/007 |
| 12,343,146 B2 * | 7/2025 | Blanchard | .......... | A61B 5/15003 |
| 2012/0197200 A1 * | 8/2012 | Belson | ................ | A61M 25/065 604/164.12 |
| 2016/0051174 A1 | 2/2016 | Devgon | | |
| 2019/0021640 A1 | 1/2019 | Burkholz et al. | | |
| 2019/0022367 A1 | 1/2019 | Burkholz et al. | | |

(Continued)

*Primary Examiner* — May A Abouelela
(74) *Attorney, Agent, or Firm* — The Webb Law Firm

(57)     ABSTRACT

A system for blood draw including a catheter adapter having a catheter and a side inlet defining a fluid pathway into and out of the catheter. The system also includes a near-patient access port member having a main branch with a distal end couplable to the side inlet and a proximal end having a needle access connector coupled thereto. The system further includes a blood draw device removably couplable to the near-patient access port member, wherein the blood draw device includes a cannula configured to penetrate the needle access connector, a flow tube configured to be advanced and retracted through the cannula, and a tube advancement tab coupled to the flow tube and configured to linearly advance and retract the flow tube through the cannula such that the flow tube may be selectively directed through the blood draw device, the near-patient access port member, and the catheter adapter.

20 Claims, 11 Drawing Sheets

(56) References Cited

U.S. PATENT DOCUMENTS

| | | | |
|---|---|---|---|
| 2019/0321590 A1* | 10/2019 | Burkholz | A61M 5/14 |
| 2020/0016374 A1 | 1/2020 | Burkholz et al. | |
| 2020/0023166 A1 | 1/2020 | Burkholz et al. | |
| 2020/0023176 A1* | 1/2020 | Hu | A61M 25/0097 |
| 2020/0046948 A1* | 2/2020 | Burkholz | A61M 25/0606 |
| 2020/0100716 A1* | 4/2020 | Devgon | A61B 5/15003 |
| 2020/0316346 A1 | 10/2020 | Burkholz et al. | |
| 2021/0068731 A1* | 3/2021 | Kumar | A61B 5/150992 |
| 2021/0068732 A1* | 3/2021 | Yan | A61B 5/150221 |
| 2021/0228842 A1 | 7/2021 | Scherich et al. | |
| 2021/0290901 A1* | 9/2021 | Burkholz | A61B 5/150015 |
| 2021/0299429 A1* | 9/2021 | Naidu | A61B 5/150992 |
| 2022/0016407 A1* | 1/2022 | Hu | A61B 5/150992 |
| 2022/0047195 A1* | 2/2022 | Ma | A61B 5/150519 |
| 2022/0080158 A1 | 3/2022 | McLaughlin et al. | |
| 2022/0161003 A1* | 5/2022 | Cook | A61B 5/15003 |
| 2022/0225913 A1* | 7/2022 | Naidu | A61B 5/150496 |
| 2022/0225914 A1* | 7/2022 | Chen | A61M 25/09041 |
| 2023/0301567 A1* | 9/2023 | Chen | A61B 5/15003 |
| 2023/0309878 A1* | 10/2023 | Burkholz | A61B 5/150992 |
| 2023/0397859 A1* | 12/2023 | Yan | A61B 5/150221 |
| 2023/0398326 A1* | 12/2023 | Jiang | A61M 25/065 |

* cited by examiner

VASCULAR ACCESS DEVICE BLOOD DRAW SYSTEM WITH SEPTUM ACCESS

CROSS-REFERENCE TO RELATED APPLICATION

The present application claims priority to U.S. Provisional Application Ser. No. 63/301,749, entitled "Vascular Access Device Blood Draw System with Septum Access" filed Jan. 21, 2022, the entire disclosure of which is hereby incorporated by reference in its entirety.

BACKGROUND OF THE INVENTION

Field of the Invention

The present disclosure generally relates to vascular access devices (VAD), blood draw devices, and related assemblies, systems, and methods for use with, e.g., a peripheral intravenous catheter (PIVC). The VAD and blood draw devices are each configured for needle access via, e.g., a septum-type needle access port on the VAD.

Description of Related Art

A catheter is commonly used to infuse fluids into vasculature of a patient. For example, the catheter may be used for infusing normal saline solution, various medicaments, or total parenteral nutrition. Furthermore, the catheter may also be used for withdrawing blood from the patient.

The catheter may be an over-the-needle peripheral intravenous catheter (PIVC). In this case, the catheter may be mounted over an introducer needle having a sharp distal tip. The catheter and the introducer needle may be assembled so that the distal tip of the introducer needle extends beyond the distal tip of the catheter with the bevel of the needle facing up away from skin of the patient. The catheter and introducer needle are generally inserted at a shallow angle through the skin into vasculature of the patient. After proper placement of the needle, the clinician may temporarily occlude flow in the vasculature and remove the needle, leaving the catheter in place (i.e., "indwelled") for future blood withdrawal and/or fluid infusion.

While PIVCs may be used for blood withdrawal, they are not typically designed and optimized for such purposes. Accordingly, several blood draw devices have been developed for use with PIVCs to improve blood collection. These devices (such as, e.g. PIVO™ from Velano Vascular Inc.) are configured as single-use devices which temporarily attach to a PIVC to draw a blood sample. Using an existing peripheral intravenous line as a conduit to the vasculature, the blood draw device advances a flexible, internal flow tube through the PIVC, beyond the catheter tip, and into the vein to collect a blood sample. This flow tube is designed to extend beyond any suboptimal draw conditions around the indwelling line to reach vein locations where blood flow is optimal for aspiration. Once blood collection is complete, the flow tube is retracted, and the device is removed from the PIVC and discarded.

In order to accommodate such blood draw devices, PIVCs having an integrated extension set have been developed. These integrated vascular access devices (VADs) typically may include extension tubing that is integrated at one end into a catheter adapter, an access port (e.g., a luer connector) coupled to the other end, and a side port to facilitate blood draw. One such integrated VAD is disclosed in U.S. patent application Ser. No. 17/143,979, which is incorporated herein by reference in its entirety. To attach the blood draw device to the integrated VAD, a coupler mechanism such as, e.g., a male luer fitting or luer lock threaded collar is generally utilized, with the blood draw device having a blunt plastic cannula and/or luer distal connector to provide the coupling. However, in certain regions of the world, the use of such coupler mechanisms (e.g., luer connectors, etc.) is not common in medical settings. Instead, these regions typically utilize needle access-type connectors, pro re nata (PRN) connectors, etc., which may be incompatible with many modern blood draw devices.

SUMMARY OF THE INVENTION

Accordingly, the present disclosure generally relates to assemblies, systems, and methods including integrated VADs having a near-patient access port with a needle access septum and a tubing advancement-compatible fluid path, as well as blood draw devices having a distal access port connector compatible with a septum-type needle access port of the VAD.

In accordance with an embodiment of the present disclosure, a system for blood draw is disclosed including a catheter adapter having a catheter configured to be inserted into a patient's vasculature and a side inlet defining a fluid pathway into and out of the catheter, and a near-patient access port member having a main branch including a distal end couplable to the side inlet of the catheter adapter and a proximal end having a needle access connector coupled thereto. The system also includes a blood draw device removably couplable to the near-patient access port member, wherein the blood draw device includes a cannula configured to penetrate the needle access connector of the near-patient access port member, a flow tube configured to be advanced and retracted through the cannula, and a tube advancement tab coupled to the flow tube and configured to linearly advance and retract the flow tube through the cannula such that the flow tube may be selectively directed through the blood draw device, the near-patient access port member, and the catheter adapter when the cannula of the blood draw device penetrates the needle access connector of the near-patient access port member.

In some embodiments, the needle access connector includes a septum.

In some embodiments, the septum is external to the main branch of the near-patient access port member.

In some embodiments, the septum is integrated within the main branch of the near-patient access port member.

In some embodiments, the septum includes an angled distal face within an interior of the main branch.

In some embodiments, the cannula is one of a sharp metal needle, a blunt metal needle, or a blunt plastic cannula.

In some embodiments, the blood draw device further includes a distal connector interface configured to removably couple the blood draw device to the near-patient access port member.

In some embodiments, the distal connector interface includes a pair of connector clips.

In some embodiments, the distal connector interface is configured to at least partially surround the cannula and form a safety shield around at least a portion of the cannula.

In some embodiments, the blood draw device further includes a safety shield configured to surround the cannula and be selectively removable from the cannula.

In some embodiments, the near-patient access port member further includes a side branch and an extension set coupled to the near-patient access port member via the side branch.

In some embodiments, the side branch is distally-directed relative to the main branch.

In some embodiments, the side branch is proximally-directed relative to the main branch.

In accordance with another aspect of the disclosure, a system for blood draw is disclosed, the system including a catheter adapter having a catheter configured to be inserted into a patient's vasculature and a side inlet defining a fluid pathway into and out of the catheter, and a near-patient access port member having a main branch including a distal end portion couplable to the side inlet of the catheter adapter and a proximal end portion having integrated septum therein. The system also includes a blood draw device removably couplable to the near-patient access port member, wherein the blood draw device includes a cannula configured to penetrate the integrated septum of the near-patient access port member, a flow tube configured to be advanced and retracted through the cannula, and a tube advancement tab coupled to the flow tube and configured to linearly advance and retract the flow tube through the cannula such that the flow tube may be selectively directed through the blood draw device, the near-patient access port member, and the catheter adapter when the cannula of the blood draw device penetrates the integrated septum of the near-patient access port member.

In some embodiments, the integrated septum includes an angled distal face within an interior of the main branch.

In some embodiments, the cannula is one of a sharp metal needle, a blunt metal needle, or a blunt plastic cannula.

In some embodiments, the blood draw device further includes a distal connector interface configured to removably couple the blood draw device to the near-patient access port member, and the distal connector interface includes a pair of connector clips.

In accordance with another aspect of the disclosure, a system for blood draw is disclosed, the system including a catheter adapter having a catheter configured to be inserted into a patient's vasculature, a proximal access port having an integrated septum positioned therein, and a side inlet, wherein both the proximal access port and the side inlet define a fluid pathway into and out of the catheter. The system further includes a near-patient access port member having a main branch including a distal end portion couplable to the side inlet of the catheter adapter and a proximal end portion, and a blood draw device removably couplable to the proximal access port of the catheter adapter, wherein the blood draw device includes a cannula configured to penetrate the integrated septum of the catheter adapter, a flow tube configured to be advanced and retracted through the cannula, and a tube advancement tab coupled to the flow tube and configured to linearly advance and retract the flow tube through the cannula such that the flow tube may be selectively directed through the blood draw device and the catheter adapter when the cannula of the blood draw device penetrates the integrated septum of the catheter adapter.

In some embodiments, the cannula is a blunt cannula.

In some embodiments, the blood draw device further includes a distal connector interface configured to removably couple the blood draw device to the proximal access port of the catheter adapter.

Further details and advantages of the invention will become clear upon reading the following detailed description in conjunction with the accompanying drawing figures, wherein like parts are designated with like reference numerals throughout.

DESCRIPTION OF PREFERRED EMBODIMENTS

Figure 1:
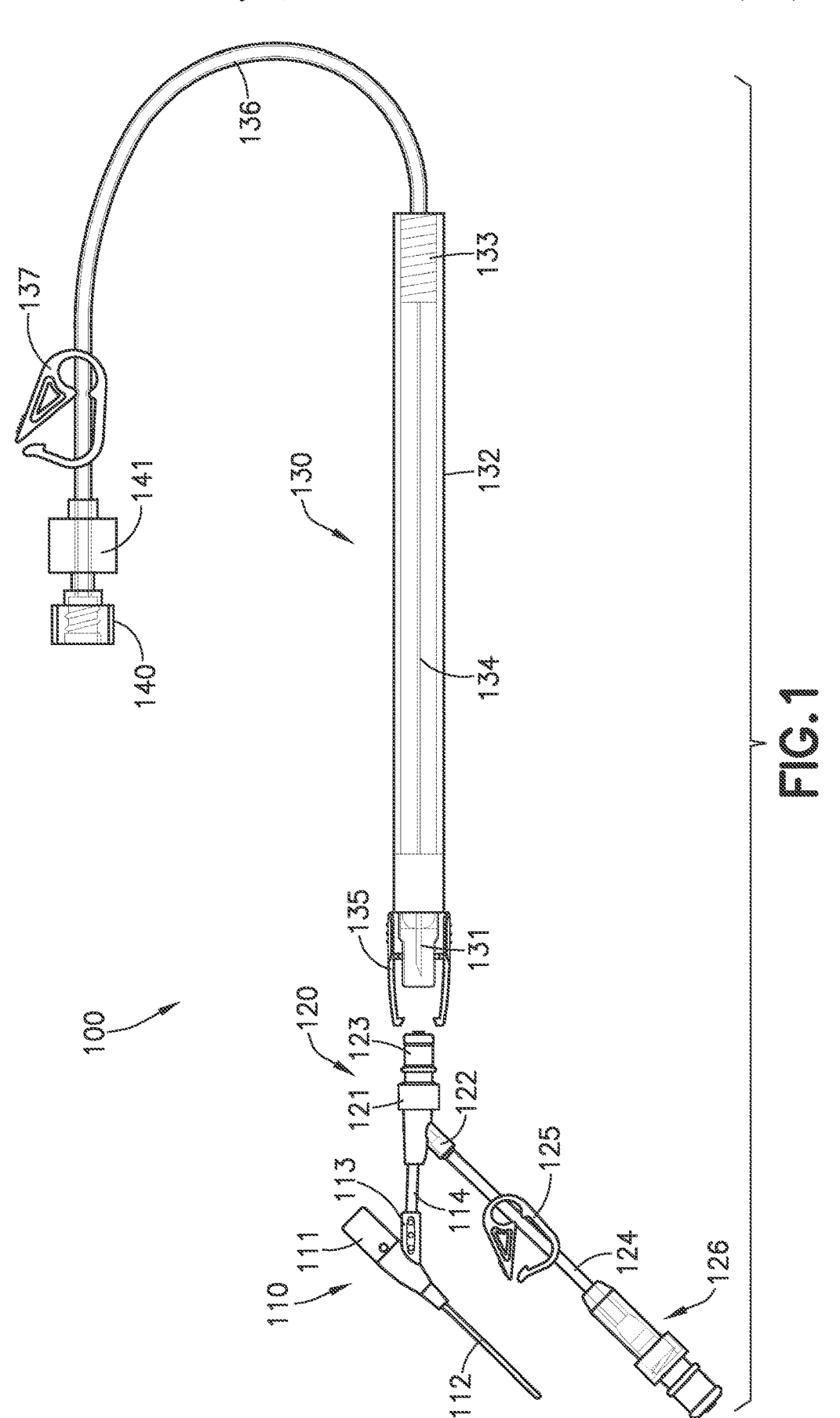
FIG. 1 is a top plan view of a vascular access device and blood draw device in accordance with an aspect of the present disclosure.

The following description is provided to enable those skilled in the art to make and use the described aspects contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present disclosure.

For the purposes of the description hereinafter, the terms "upper", "lower", "right", "left", "vertical", "horizontal", "top", "bottom", "lateral", "longitudinal", and derivatives thereof shall relate to the invention as it is oriented in the drawings. However, it is to be understood that the invention may assume various alternative variations, except where expressly specified to the contrary. It is also to be understood that the specific devices illustrated in the attached drawings, and described in the following specification, are simply exemplary aspects of the invention. Hence, specific dimensions and other physical characteristics related to the aspects disclosed herein are not to be considered as limiting.

Embodiments of the present disclosure will primarily be described in the context of integrated VADs. However, embodiments of the present disclosure equally extend to other IV catheters. Accordingly, the techniques of the present disclosure can be applied to any type of integrated IV catheter. For purposes of the specification and the claims, an integrated IV catheter should be construed as an IV catheter that includes an integrated extension set.

Referring to FIG. 1, a VAD system 100 in accordance with an aspect of the present disclosure is shown. VAD system 100 includes a catheter adapter 110 from which a catheter 112 distally extends from an adapter body 111. While not shown in FIG. 1, in some embodiments, the catheter adapter 110 may include, e.g., a flexible stabilization platform. The catheter adapter 110 also includes a side inlet 113 which defines a fluid pathway into (and out of) the catheter 112. It is to be understood that the exact configuration and function of catheter adapter 110 is not essential to the present disclosure, and any suitable configuration and/or interaction of these components may be employed.

VAD system 100 also includes a near-patient access port member 120. The near-patient access port member 120 has two fluid pathways comprising a main branch 121 and a side branch 122. The main branch 121 is coupled to the side inlet 113 of catheter adapter 110 via intermediate tubing 114. However, in some embodiments, it is to be understood that main branch 122 may be coupled directly to side inlet 113, thereby obviating the need for intermediate tubing 114.

The side branch 122 is configured couple an extension set with the near-patient access port member 120. As depicted, extension set includes extension tubing 124 that extends between side branch 122 and an access port 126, and may include a pinch clamp 125 for occluding extension tubing 124. In some embodiments, the access port 126 may include a PRN, needle-less access connector (NAC), or integrated (non-removable) PRN or NAC connector. Furthermore, while access port 126 is shown in FIG. 1 as having a single port, it is to be understood that access port 126 may be configured to have dual ports. In this way, the extension set provides a means of fluid infusion via the VAD system 100.

As shown in FIG. 1, side branch 122 may be configured as a Y-type branch relative to main branch 121, extending at an angle of, e.g., between 30° and 150°. However, in some embodiments, the side branch 122 may be configured as a T-type branch, extending substantially perpendicular (i.e., 90°) to the main branch 121.

A proximal end of near-patient access port member 120 includes a needle access connector 123. The needle access connector 123 may be configured for use with needles or other cannula, and may be, e.g., a PRN or other septum. However, it is to be understood that needle access connector 123 may be configured as any suitable connector capable of interfacing with a cannula. Needle access connector 123 may be removably coupled to the main branch 121 or, in some embodiments, may be bonded or otherwise affixed to the main branch 121 of near-patient access port member 120.

Referring still to FIG. 1, the VAD system 100 also includes a blood draw device 130. Blood draw device 130 includes a body 132, a tube advancement tab 133, and a flow tube 134 extending therethrough. The tube advancement tab 133 is slidably coupled to the body 132 and is also coupled to a proximal end of flow tube 134. As such, manual longitudinal movement of the tube advancement tab 133 along the body 132 results in corresponding longitudinal movement of flow tube 134 within the body 132. However, while blood draw device 130 is shown and described utilizing a tube advancement tab 133 to longitudinally direct the flow tube 134, it is to be understood that other user-operated advancement mechanisms such as, e.g., rotary mechanisms, etc., may be utilized to advance and/or retract the flow tube 134 in accordance with other embodiments.

Blood draw device 130 may include an extension tube 136 coupled to a proximal end thereof, with extension tube 136 being fluidly coupled to flow tube 134. A pinch clamp 137 may be provided for occluding extension tube 136. Furthermore, the proximal end of extension tube 136 may be coupled to an end coupling device 140 and adapter member 141. End coupling device 140 may be, e.g., an end cap, luer lock access device, or any other appropriate coupling device for connection to a blood collection (or fluid administration) device, while adapter member 141 may be configured as, e.g., a luer adapter. In this way, the blood draw device 130 may be fluidly coupled to a blood collection device including, e.g., a evacuated blood collection tube, so as to allow blood to be drawn through the blood draw device 130 via the catheter adapter 110 and near-patient access port member 120.

Blood draw device 130 further includes a cannula 131 extending from a distal end thereof. The cannula 131 may be any appropriate device capable of piercing a needle access connector (e.g., a septum) such as, e.g., a sharp metal needle, a blunt metal needle, a blunt plastic cannula, etc. The cannula 131 is sized such that the flow tube 134 may selectively pass therethrough. The blood draw device 130 also includes a distal connector interface 135. In some embodiments, the distal connector interface 135 at least partially surrounds the cannula 131 and includes a pair of connector clips so as to allow the blood draw device 130 to be releasably secured to the near-patient access port member 120, as will be described in further detail below. However, it is to be understood that distal connector interface 135 is not limited to such an arrangement, and may be any appropriate connector such as, e.g., a slip or threaded luer, etc.

Figure 2A:
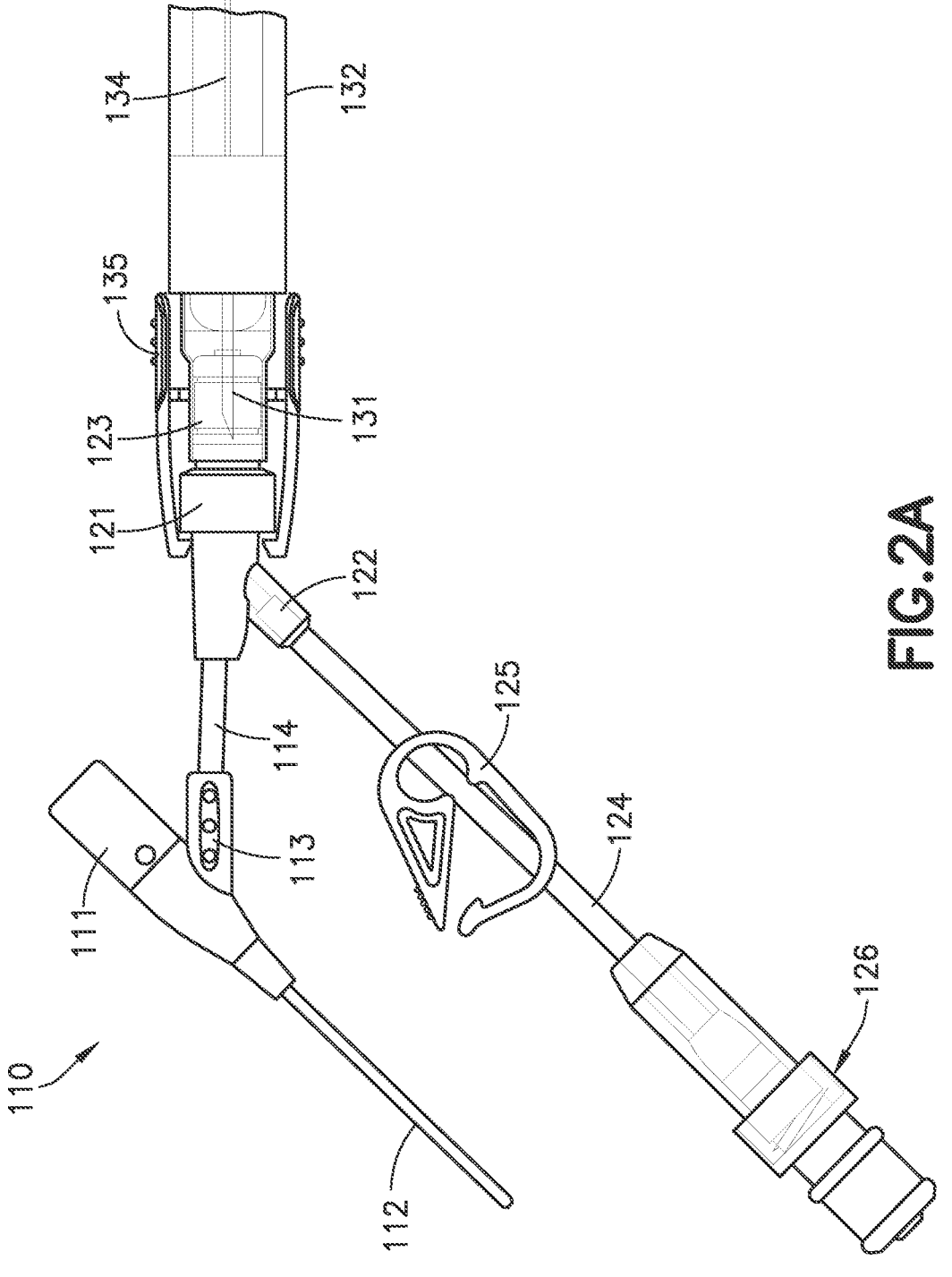
FIG. 2A is a partial top plan view of the vascular access device and blood draw device of FIG. 1 in a first configuration.
Figure 2B:
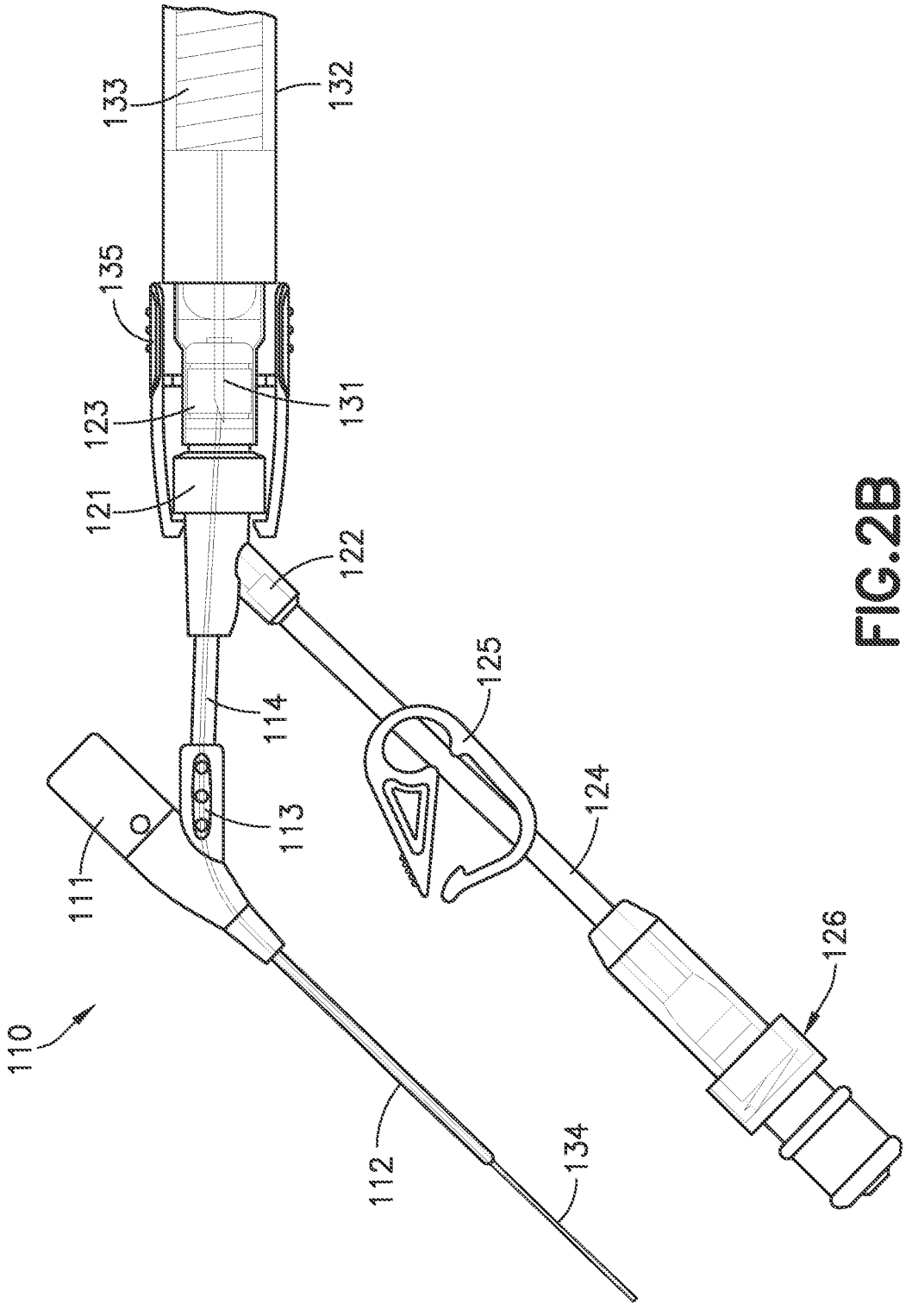
FIG. 2B is a partial top plan view of the vascular access device and blood draw device of FIG. 1 in a second configuration.

Referring to FIGS. 2A and 2B, blood draw device 130 is shown as coupled to the near-patient access port member 120. Specifically, as shown in FIG. 2A, the distal connector interface 135 is coupled to the main branch 121 of the near-patient access port member 120 by way of, e.g., securement of a pair of connector clips to a corresponding surface of the main branch 121. In providing this attachment, the cannula 131 is able to pierce the needle access connector 123 such that the blood draw device 130 is fluidly coupled to the near-patient access port member 120 and, thus, is also fluidly coupled to the catheter adapter 110.

As shown in FIG. 2B, as the user manipulates the tube advancement tab 133 of the blood draw device 130 distally, the flow tube 134 correspondingly passes through the cannula 131, the main branch 121 of near-patient access port member 120, the intermediate tubing 114, the side inlet 113, and, finally, the catheter 112. The length of the flow tube 134 is configured such that a predetermined length of flow tube 134 is in an advanced position, extending beyond the distal end of catheter 112 when tube advancement tab 133 is moved to its most distal position along body 132 of blood draw device 130, thereby providing a conduit for blood draw which extends into the patient's vasculature beyond the indwelling catheter 112.

While not shown in FIGS. 2A and 2B, it is to be understood that the flow tube 134 can be retracted by proximal movement of the tube advancement tab 133 after a blood draw procedure is completed. With the flow tube 134 in a retracted position, the distal connector interface 135 can be disconnected from the near-patient access port member 120, thereby allowing the cannula 131 to be withdrawn from the needle access connector 123. In some embodiments, once disconnected from the near-patient access port member 120, the blood draw device 130 can be discarded in an appropriate medical waste container.

Figure 3:
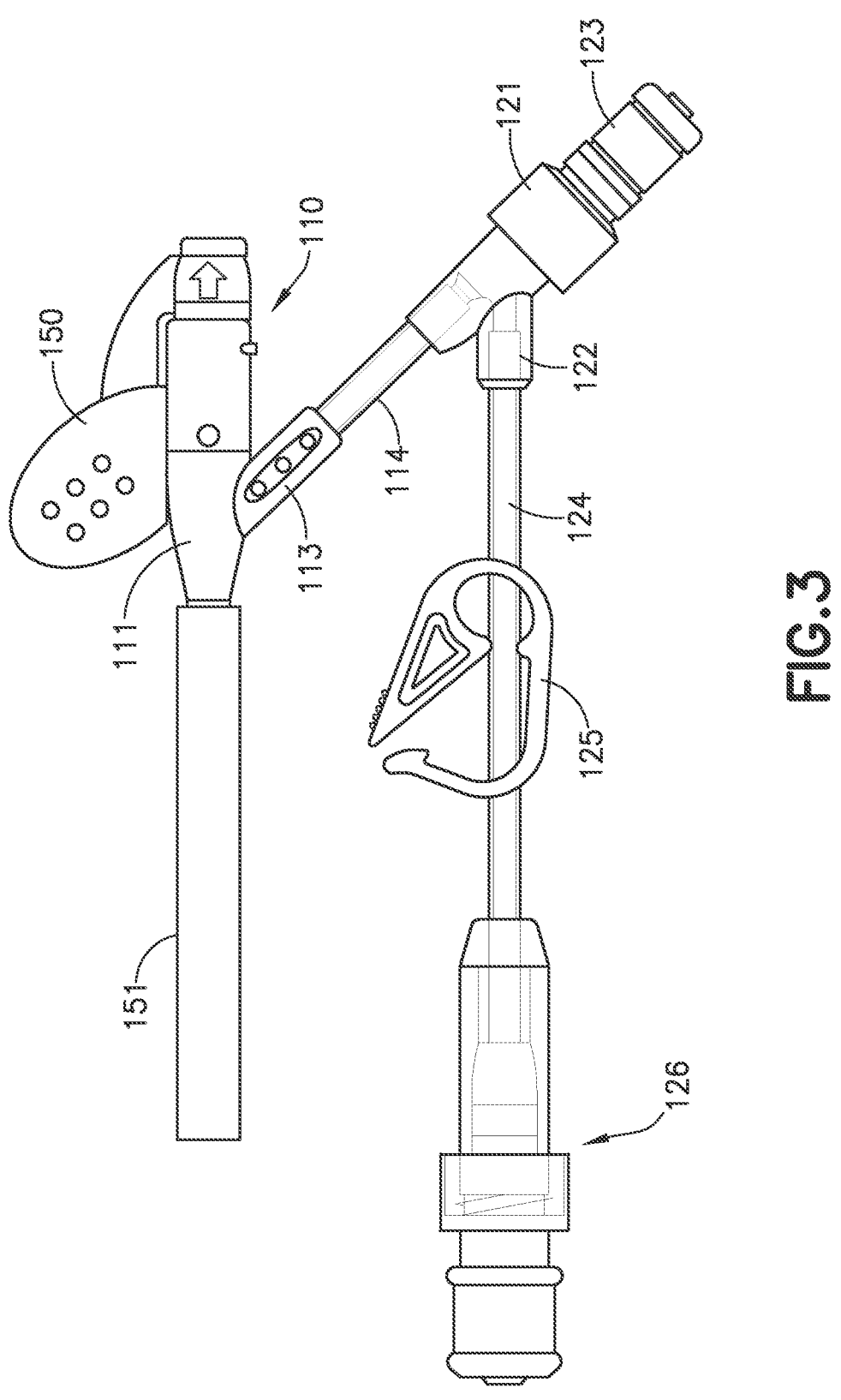
FIG. 3 is a top plan view of a vascular access device in accordance with another aspect of the present disclosure.

Next, referring to FIG. 3, in some embodiments, the catheter adapter 110 may be provided with a needle hub grip 150. While not shown in FIG. 3, in some embodiments, the catheter adapter 110 may include a stabilization platform, which enables the catheter adapter 110 to be stabilized on the patient's skin at the insertion location of the catheter 112, resisting rotation or other movement of the catheter adapter 110. Furthermore, a sleeve 151 may be provided over at least a portion of the catheter 112 prior to use of the catheter adapter 110, during storage, transport, etc. At the time of use, the sleeve 151 can be removed to expose the catheter 112.

Figure 4:
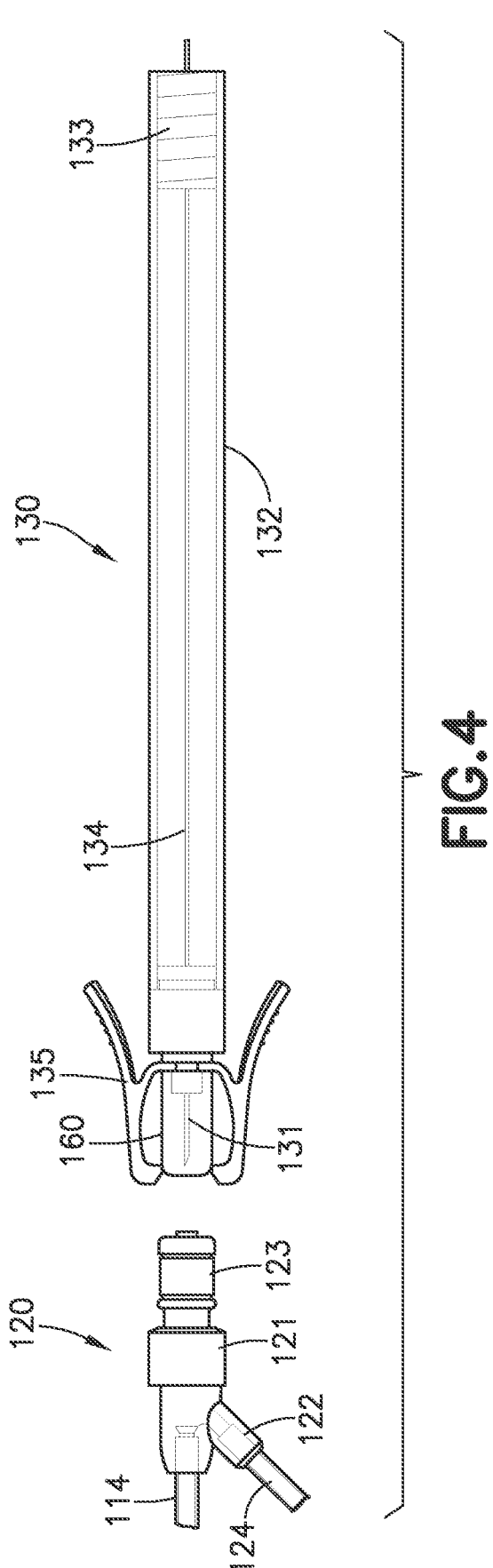
FIG. 4 is a partial top plan view of a vascular access device and blood draw device in accordance with another aspect of the present disclosure.

Referring now to FIG. 4, in accordance with another aspect of the present disclosure, the blood draw device 130 may include a safety shield 160 configured to be positioned over the cannula 131 so as to prevent accidental needle stick injuries, etc. In some embodiments, the safety shield 160 is non-removable, providing protection as the device is used and the blood draw device 130 is removed from the catheter 112. In other embodiments, the safety shield 160 may be selectively removable by the user prior to coupling the blood draw device 130 to the near-patient access port member 120. For example, the safety shield 160 may be coupled to the blood draw device 130 by way of, e.g., a press-fit connection, a threaded connection, etc., thereby allowing the user to manually remove the safety shield 160 prior to use. Alternatively, the safety shield 160 may be formed of a flexible or otherwise collapsible material, thereby enabling the safety shield 160 to collapse or fold when the blood draw device 130 is pressed toward the near-patient access port member 120, thereby allowing the cannula 131 to penetrate the needle access connector 123 without user exposure to the cannula 131. In some embodiments, upon removal of the blood draw device 130 from the near-patent access port member 120, the safety shield 160 can be configured to automatically return to a covering position over the cannula 131, thereby reducing the user exposure to the cannula 131 after blood collection via the blood draw device 130.

Figure 5A:
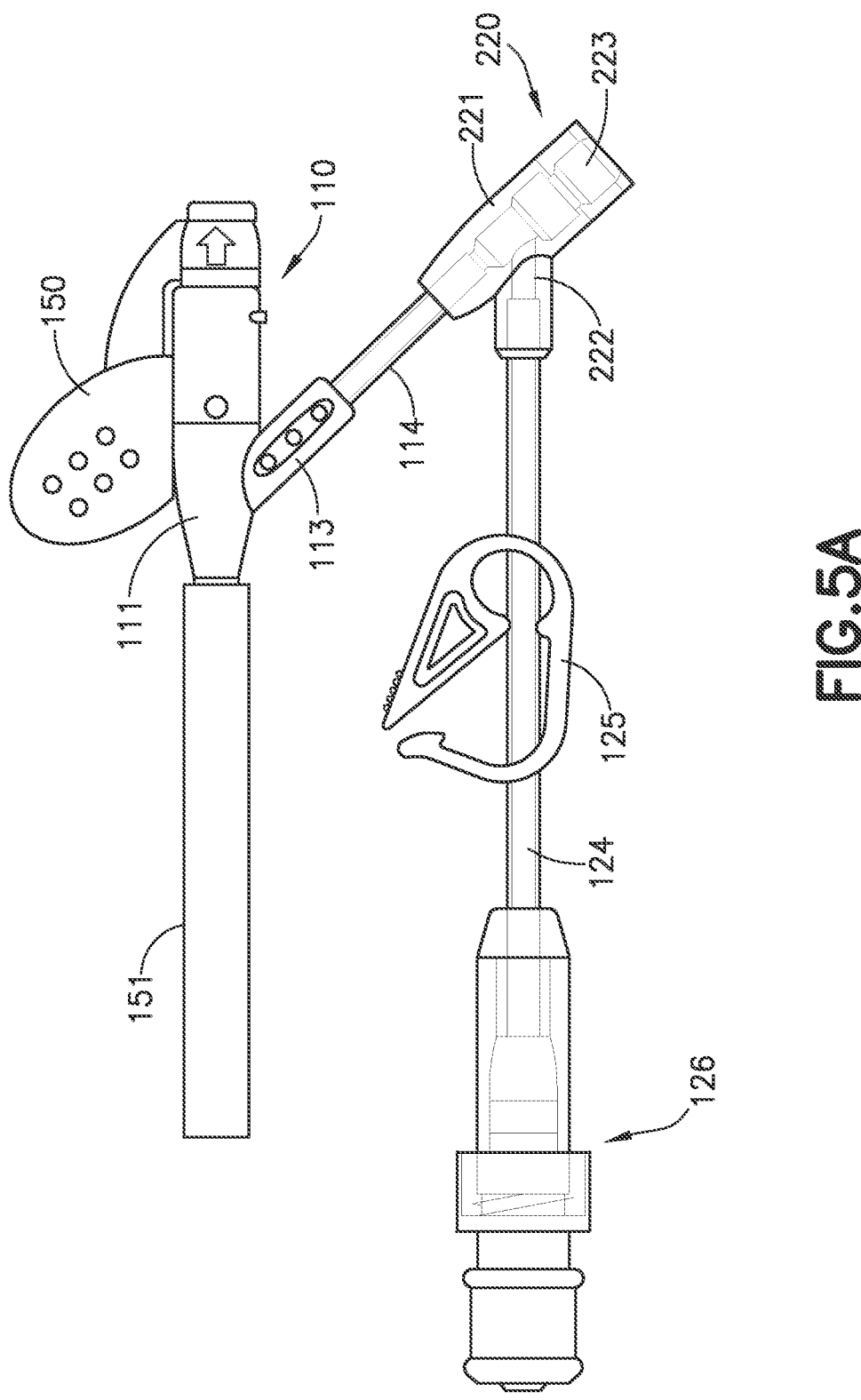
FIG. 5A is a top plan view of a vascular access device in accordance with another aspect of the present disclosure.
Figures 5B, 5C:
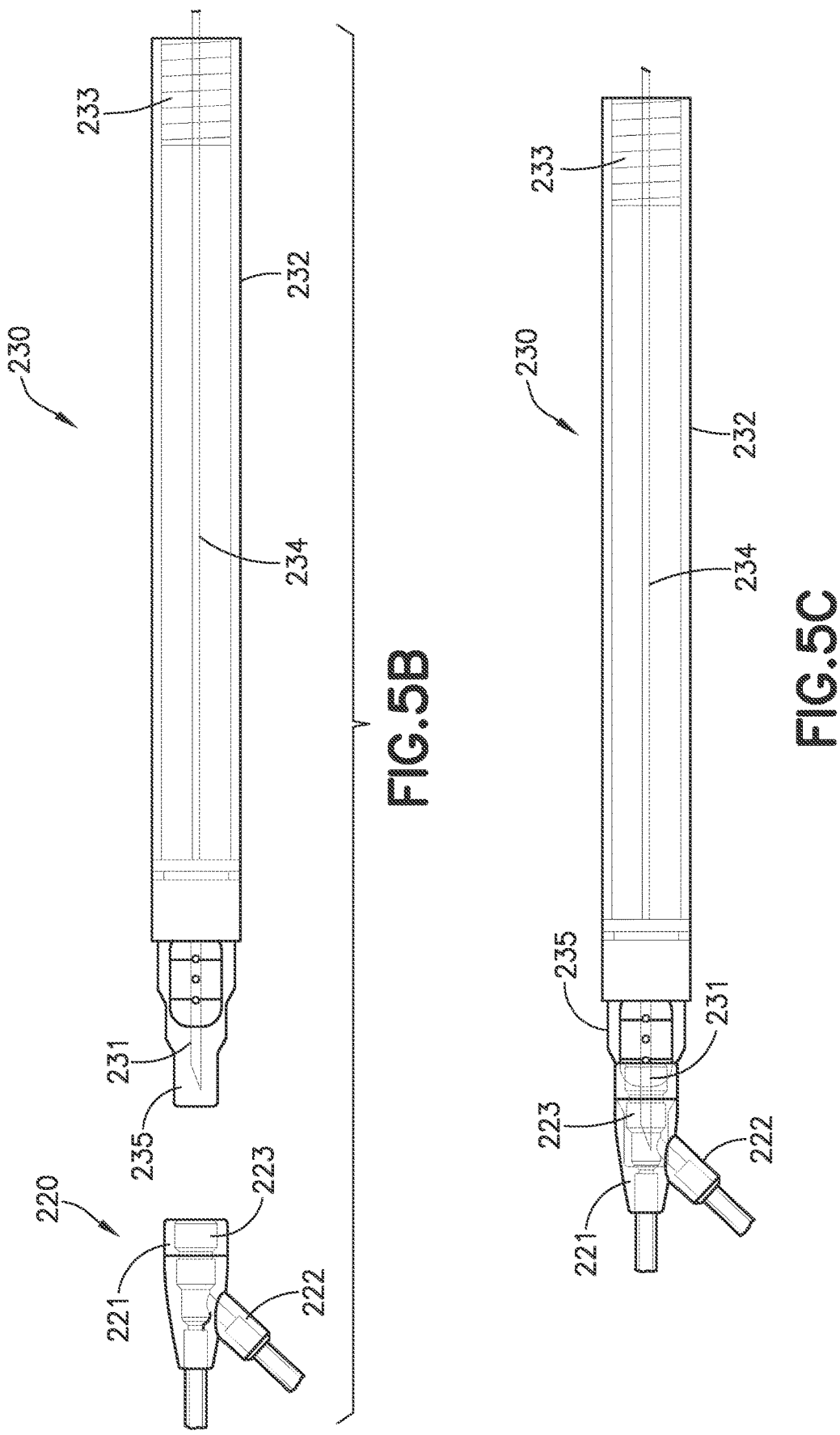
FIG. 5B is a top plan view of a blood draw device for use with the vascular access device of FIG. 5A in a first configuration.
FIG. 5C is a top plan view of a blood draw device for use with the vascular access device of FIG. 5A in a second configuration.

Next, referring to FIGS. 5A-5C, a near-patient access port member 220 and a blood draw device 230 in accordance with another aspect of the present disclosure are shown. Near-patient access port member 220 is substantially similar to near-patient access port member 120 described above, with near-patient access port member 220 having two fluid pathways comprising a main branch 221 and a side branch 222. The main branch 221 may be coupled to the side inlet 113 of catheter adapter 110 via, e.g., intermediate tubing 114. In some embodiments, the side branch 222 may be configured as a Y-type branch relative to main branch 221, extending at an angle of, e.g., between 30° and 150° to be either distally-facing or proximally-facing. Specifically, in the embodiment shown in FIGS. 5A-5C, the side branch 222 is proximally-facing and extends from the main branch 221 at an angle of about 45°. With this configuration, the junction formed within the near-patient access port member 220 can be effectively flushed via the access port 126 and extension tubing 124. However, in some embodiments, the side branch 222 may be configured as a T-type branch, extending substantially perpendicular (i.e., 90°) to the main branch 221.

Near-patient access port member 220 further includes an integrated, puncturable septum 223. Thus, unlike needle access connector 123, which was external to the main branch 121 of near-patient access port member 220, septum 223 is internal to (and, thus, integrated with) the main branch 221 of near-patient access port member 220.

Referring to FIGS. 5B and 5C, the blood draw device 230 includes a body 232, a tube advancement tab 233, and a flow tube 234 extending therethrough. The tube advancement tab 233 is slidably coupled to the body 232 and is also coupled to a proximal end of flow tube 234. As such, manual longitudinal movement of the tube advancement tab 233 along the body 232 results in corresponding longitudinal movement of flow tube 234 within the body 232. While not shown in FIGS. 5B and 5C, it is to be understood that blood draw device 230 may be fluidly coupled to a blood collection device including, e.g., a evacuated blood collection tube, so as to allow blood to be drawn through the blood draw device 230 via the catheter adapter 110 and near-patient access port member 220.

Blood draw device 230 further includes a cannula 231 extending from a distal end thereof. The cannula 231 may be any appropriate device capable of piercing septum 223 such as, e.g., a sharp metal needle, a blunt metal needle, a blunt plastic cannula, etc. The cannula 231 is sized such that the flow tube 234 may selectively pass therethrough.

The blood draw device 230 also includes a distal connector interface 235. The distal connector interface 235 at least partially surrounds the cannula 231 so as to serve as a needle safety shield, aiding in the prevention of accidental needle stick injuries. Additionally, the distal connector interface 235 may include one or more clips so as to allow the blood draw device 230 to be releasably secured to the near-patient access port member 220, as is shown in FIG. 5C. When secured to the near-patient access port member 220, the cannula 231 of the blood draw device 230 is configured to penetrate the septum 223, thereby providing a fluid connection between the near-patient access port member 220 and the blood draw device 230, as well as a conduit through which the flow tube 234 can be advanced and retracted in a manner similar to that described above with respect to FIG. 2B.

Figure 6:
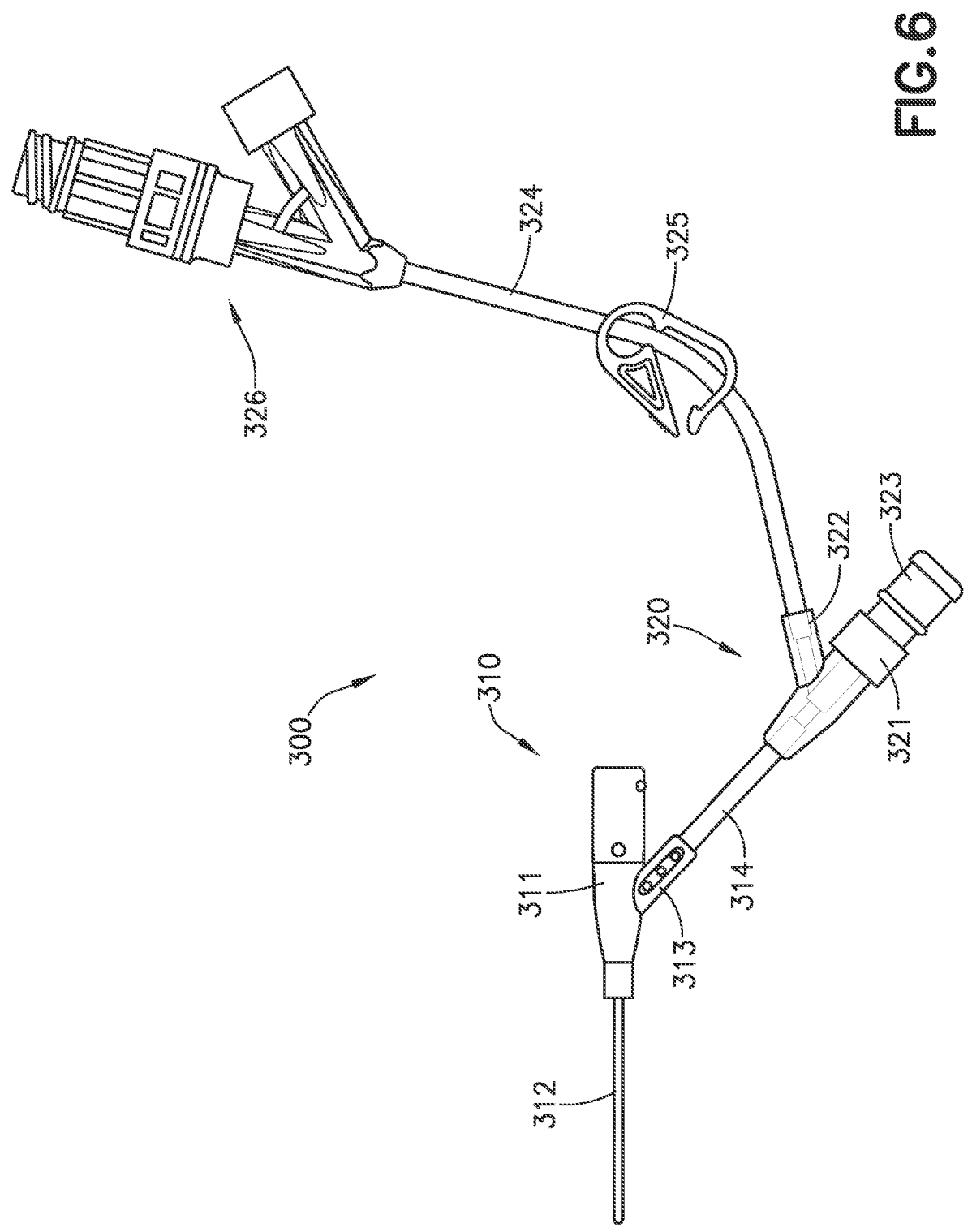
FIG. 6 is a top plan view of a vascular access device in accordance with another aspect of the present disclosure.

Referring now to FIG. 6, a VAD system 300 in accordance with another aspect of the present disclosure is shown. VAD system 300 includes a catheter adapter 310 from which a catheter 312 distally extends from an adapter body 311. While not shown in FIG. 6, in some embodiments, the catheter adapter 310 may include, e.g., a flexible stabilization platform. The catheter adapter 310 also includes a side inlet 313 which defines a fluid pathway into (and out of) the catheter 312.

VAD system 300 also includes a near-patient access port member 320. The near-patient access port member 320 has two fluid pathways comprising a main branch 321 and a side branch 322. The main branch 321 is coupled to the side inlet 313 of catheter adapter 310 via intermediate tubing 314. However, in some embodiments, it is to be understood that main branch 322 may be coupled directly to side inlet 313, thereby obviating the need for intermediate tubing 314.

The side branch 322 is configured couple an extension set with the near-patient access port member 320. As depicted, extension set includes extension tubing 324 that extends between side branch 322 and an access port 326, and may include a pinch clamp 325 for occluding extension tubing 324. In some embodiments, the access port 326 may include a PRN, NAC, or integrated connector. Furthermore, while access port 326 is shown in FIG. 6 as having dual ports, it is to be understood that access port 326 may be configured to have a single port. In this way, the extension set provides a means of fluid infusion via the VAD system 300.

As shown in FIG. 6, side branch 322 may be configured as a distally-facing, Y-type branch relative to main branch 321, extending at an angle of, e.g., between 20° and 160°. Accordingly, unlike the substantially proximally-facing branches shown and described above with respect to FIGS. 1-5C, the side branch 322 is configured to direct fluid or other materials from the extension tubing 324 in a distal direction relative to the main branch 321. Furthermore, it is to be understood that the location of the side branch 322 may also vary rotationally (360°) around the axis of the main branch 321.

A proximal end of near-patient access port member 320 further includes a needle access connector 323. The needle access connector 323 may be configured for use with PRN or other needles, and may be, e.g., a septum. However, it is to be understood that needle access connector 323 may be configured as any suitable connector capable of interfacing with a cannula. Needle access connector 323 may be removably coupled to the main branch 321 or, in some embodiments, may be bonded or otherwise affixed to the main branch 321 of near-patient access port member 320. While not shown in FIG. 6, it is to be understood that the near-patient access port member 320 is configured to be couplable to a blood draw device such as blood draw device 130 and/or blood draw device 230 as described above.

Figure 7:
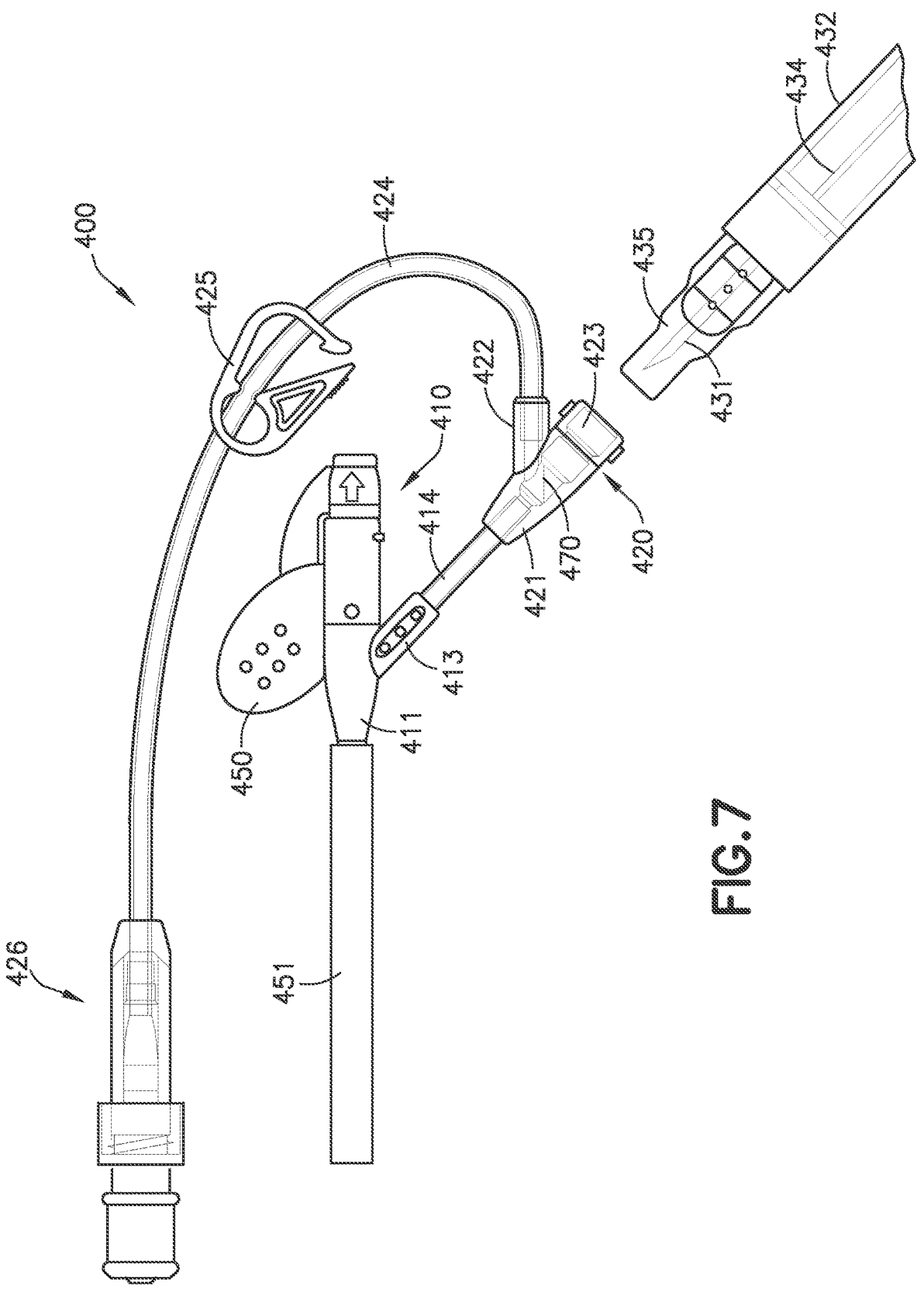
FIG. 7 is a partial top plan view of a vascular access device and blood draw device in accordance with another aspect of the present disclosure.

Next, referring to FIG. 7, a VAD system 400 in accordance with another aspect of the present disclosure is shown. As will be described in further detail below, VAD system 400 includes a near-patient access adapter port member configured for improved flushing.

VAD system 400 includes a catheter adapter 410 from which a catheter (not shown) distally extends from an adapter body 411. The catheter adapter 410 may be provided with a needle hub grip 450, which may be removed with the needle after the catheter is placed. While not shown in FIG. 7, in some embodiments, the catheter adapter 410 may include a stabilization platform, which enables the catheter adapter 410 to be stabilized on the patient's skin at the insertion location of the catheter, resisting rotation or other movement of the catheter adapter 410. Furthermore, a sleeve 451 may be provided over at least a portion of the catheter prior to use of the catheter adapter 410, during storage, transport, etc. At the time of use, the sleeve 451 can be removed to expose the catheter.

VAD system 400 also includes a near-patient access port member 420. The near-patient access port member 420 has two fluid pathways comprising a main branch 421 and a side branch 422. In the embodiment shown in FIG. 7, the main branch 421 is coupled to the side inlet 413 of catheter adapter 410 via intermediate tubing 414. The side branch 422 is configured couple an extension set with the near-patient access port member 420. As depicted, extension set includes extension tubing 424 that extends between side branch 422 and an access port 426, and may include a pinch clamp 425 for occluding extension tubing 424. In some embodiments, the access port 426 may include a PRN, NAC, or integrated connector. Furthermore, as shown in FIG. 7, side branch 422 may be configured as a distally-facing, Y-type branch relative to main branch 421, extending at an angle of, e.g., between 20° and 160°. However, it is to be understood that side branch 422 is not limited to such a configuration.

Near-patient access port member 420 further includes an integrated, puncturable septum 423, which is at least partially disposed internally within (and, thus, integrated with) the main branch 421 of near-patient access port member 420. In some embodiments, the septum 423 may include an angled distal face 470. Angled distal face 470 is configured to allow for improved flushing of the interior of the near-patient access port member 420 via the side branch 422. Alternatively and/or additionally, the septum 423 may include another flow-directing or turbulence-generating feature to provide for improved flushing. Furthermore, other features of the VAD system (400), such as the tubing, near-patient access port member, etc., may include one or more flow-directing or turbulence-generating features to provide for improved flushing (such as, e.g., an off-axis tubing extension, etc.).

Referring still to FIG. 7, a blood draw device is also provided, which includes a body 432, a tube advancement tab 433, and a flow tube 434 extending therethrough. The tube advancement tab 433 is slidably coupled to the body 432 and is also coupled to a proximal end of flow tube 434. The blood draw device further includes a cannula 431 extending from a distal end thereof. The cannula 431 may be any appropriate device capable of piercing the integrated septum 423 such as, e.g., a sharp metal needle, a blunt metal needle, a blunt plastic cannula, etc. The cannula 431 is sized such that the flow tube 434 may selectively pass therethrough.

The blood draw device 430 also includes a distal connector interface 435. The distal connector interface 435 at least partially surrounds the cannula 431 so as to serve as a needle safety shield, aiding in the prevention of accidental needle stick injuries. Additionally, the distal connector interface 435 may include one or more clips so as to allow the blood draw device to be releasably secured to the near-patient access port member 420. When secured to the near-patient access port member 420, the cannula 431 is configured to penetrate the septum 423, thereby providing a fluid connection between the near-patient access port member 420 and the blood draw device.

Figures 8A, 8B:
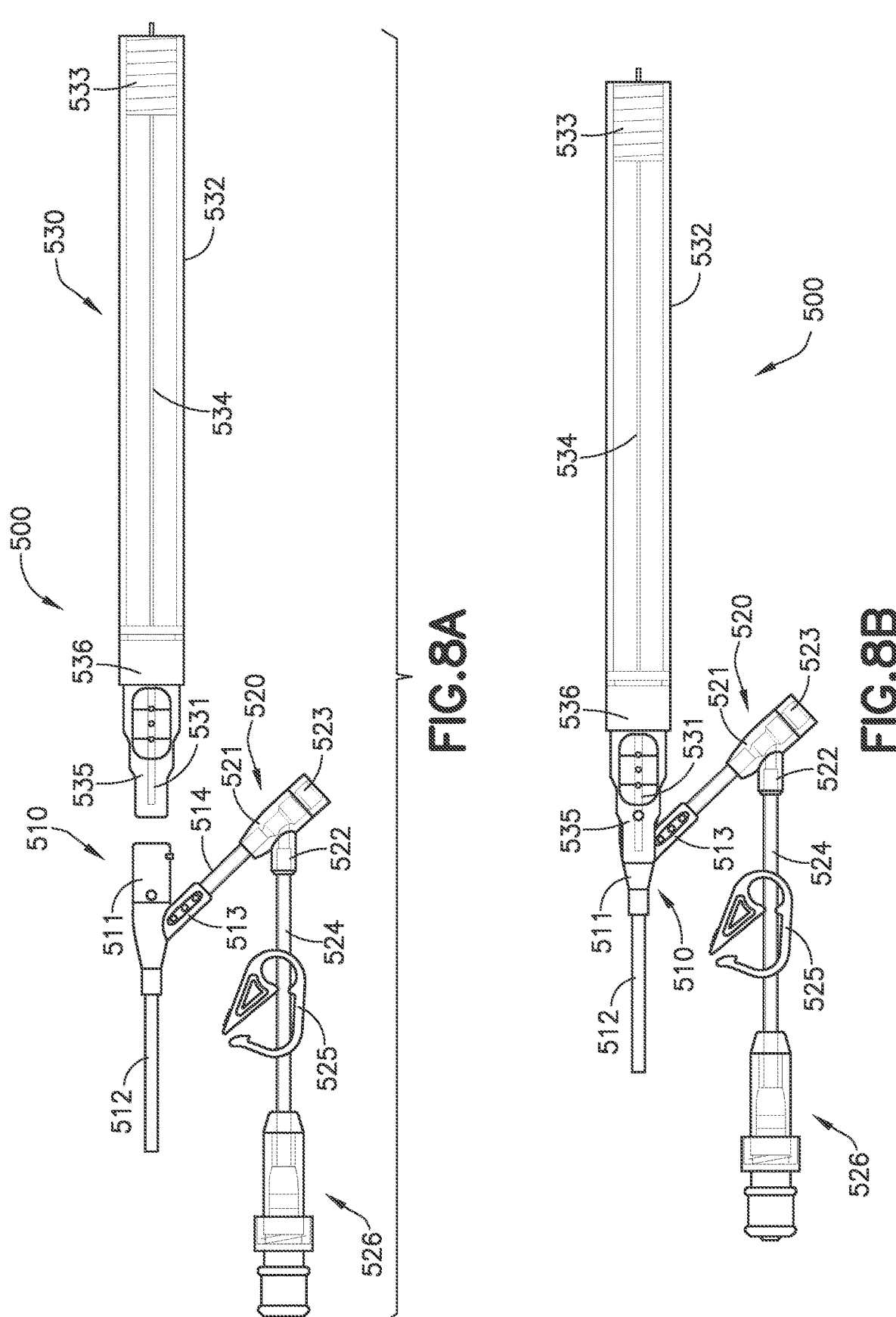
FIG. 8A is a top plan view of a vascular access device and blood draw device in accordance with another aspect of the present disclosure.
FIG. 8B is a top plan view of the vascular access device and the blood draw device of FIG. 8A in a first configuration.
Figure 8C:
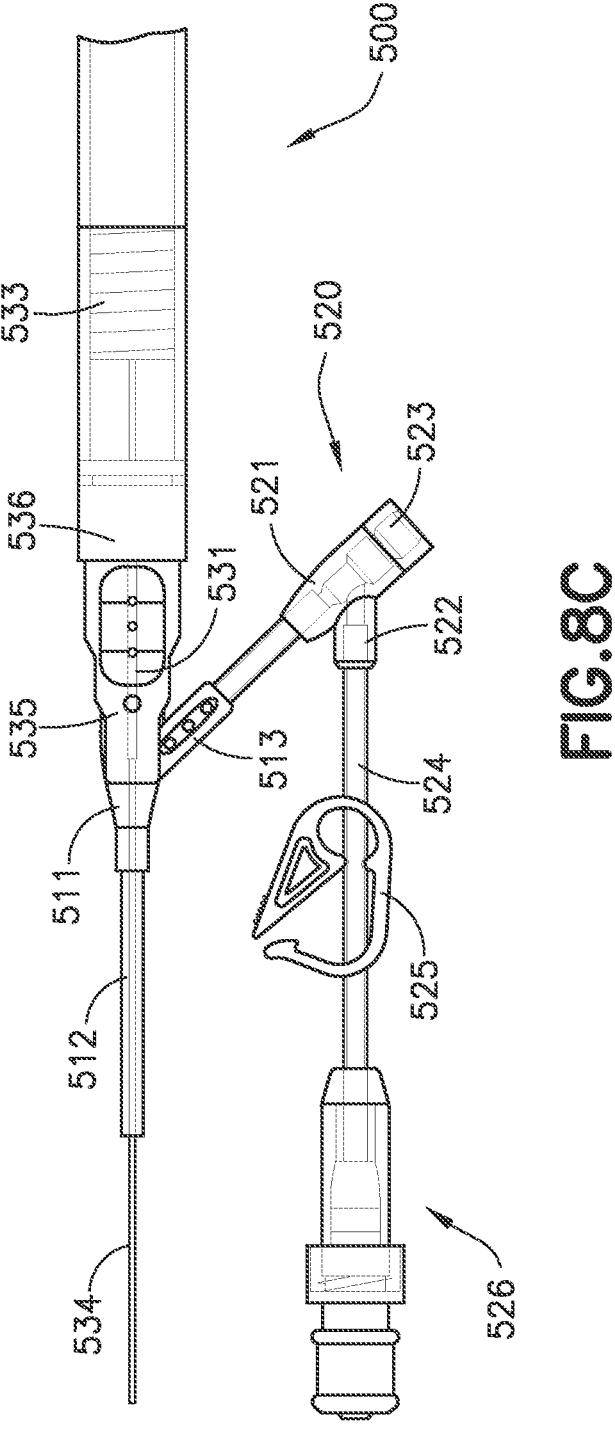
FIG. 8C is a partial top plan view of the vascular access device and the blood draw device of FIG. 8A in a second configuration.

Referring now to FIGS. 8A-8C, a VAD system 500 in accordance with another aspect of the present disclosure is illustrated. Unlike the VAD systems described herein with respect to FIGS. 1-7, which utilized a coupling between a near-patient access port member and a blood draw device for performing a blood draw, VAD system 500 utilizes a direct connection between a catheter adapter and a blood draw device.

Specifically, VAD system 500 includes a catheter adapter 510, a near-patient access port member 520, and a blood draw device 530. Near-patient access port member 520 includes two fluid pathways comprising a main branch 521 and a side branch 522. The main branch 521 may be coupled to a side inlet 513 of catheter adapter 510 via, e.g., intermediate tubing 514. In some embodiments, the side branch 522 may be configured as a Y-type branch relative to main branch 521, extending at an angle of, e.g., between 30° and 150° to be either distally-facing or proximally-facing. However, in some embodiments, the side branch 522 may be configured as a T-type branch, extending substantially perpendicular (i.e., 90°) to the main branch 521. Near-patient access port member 520 further includes an integrated, puncturable septum 523.

In some embodiments, the side branch 522 is configured couple an extension set with the near-patient access port member 520. As depicted, extension set includes extension tubing 524 that extends between side branch 522 and an access port 526, and may include a pinch clamp 525 for occluding extension tubing 524. In some embodiments, the access port 526 may include a PRN, NAC, or integrated connector.

Referring to FIGS. 8A and 8B, the blood draw device 530 includes a body 532, a tube advancement tab 533, and a flow tube 534 extending therethrough. The tube advancement tab 533 is slidably coupled to the body 532 and is also coupled to a proximal end of flow tube 534. As such, manual longitudinal movement of the tube advancement tab 533 along the body 532 results in corresponding longitudinal movement of flow tube 534 within the body 532.

Blood draw device 530 further includes a cannula 531 extending from a distal end thereof. However, unlike the cannula(s) described above with respect to FIGS. 1-7, which generally included sharp cannulas capable of piercing a septum of the near-patient access port member, cannula 531 may be configured as any cannula capable of penetrating a needle septum (not shown) integrated within a proximal access port 511 of the catheter adapter 510 itself. That is, the cannula 531 may be sharp or blunt, and may be formed of any appropriate material such as, e.g., metal or plastic. The cannula 531 is sized such that the flow tube 534 may selectively pass therethrough. The integrated needle septum within the proximal access port 511 of the catheter adapter 510 may be any appropriate septum such as, e.g., a solid, single-piece septum, a three-piece septum, or any other septum configuration capable of penetration by a cannula. In some embodiments, when accessing the needle septum, the near-patient access port member 520 is not needed. Thus, in such embodiments, the device may utilize a standard extension set without the near-patient access port.

The blood draw device 530 also includes a distal connector interface 535. The distal connector interface 535 may at least partially surrounds the cannula 531 so as to serve as a safety shield. Additionally, the distal connector interface 535 may include one or more clips so as to allow the blood draw device 530 to be releasably secured directly to the catheter adapter 510, as is shown in FIGS. 8B and 8C. When secured to the catheter adapter 510, the cannula 531 of the blood draw device 530 is configured to penetrate the septum (not shown) integrated within the catheter adapter 510, thereby providing a fluid connection between the catheter adapter 510 and the blood draw device 530, as well as a conduit through which the flow tube 534 can be advanced such that the flow tube 534 can be selectively advanced beyond the distal tip of catheter 512, as is shown in FIG. 8C.

In some embodiments, the blood draw device 530 may include a coupling 536 positioned between the body 532 and the distal connector interface 535. The coupling 536 may be a secure or pivotable coupling, and may further be configured to enable direct access to the integrated septum (not shown) within the catheter adapter 510.

While the blood draw devices described above utilize a tube advancement tab to linearly advance the flow tube, it is to be understood that other advancement mechanisms may be utilized such as, e.g., roller mechanisms, etc. Additionally, while the distal connector interfaces described above utilize connector clips, it is to be understood that any appropriate connection interface may be utilized such as, e.g., a slip luer, a threaded luer, etc.

Furthermore, it is to be understood that the flow tube of the blood draw device described in the various embodiments above may be, e.g., straight, stepped, tapered, etc., and may be formed of any appropriate material such as, e.g., TPU, polyimide, PEEK, and/or any other polymeric material. Additionally and/or alternatively, it is to be understood that the systems and devices described above are not limited to use with flow tubes. The flow tube may be replaced by, e.g., a guidewire (active or inactive), a tubing/guidewire hybrid, a sensor delivery probe, a braided expanding probe, etc.

While several embodiments of VAD systems were described in the foregoing detailed description, those skilled in the art may make modifications and alterations to these embodiments without departing from the scope and spirit of the invention. Accordingly, the foregoing description is intended to be illustrative rather than restrictive. The invention described hereinabove is defined by the appended claims and all changes to the invention that fall within the meaning and the range of equivalency of the claims are embraced within their scope.

What is claimed is:

1. A system for blood draw comprising:
a catheter adapter comprising a catheter configured to be inserted into a patient's vasculature and a side inlet defining a fluid pathway into and out of the catheter;
a near-patient access port member having a main branch comprising a distal end couplable to the side inlet of the catheter adapter and a proximal end having a needle access connector coupled thereto; and
a blood draw device removably couplable to the near-patient access port member, wherein the blood draw device comprises:
a cannula configured to penetrate the needle access connector of the near-patient access port member;
a flow tube configured to be advanced and retracted through the cannula; and
a tube advancement tab coupled to the flow tube and configured to linearly advance and retract the flow tube through the cannula such that the flow tube is selectively directable through the blood draw device, the near-patient access port member, and the catheter adapter when the cannula of the blood draw device penetrates the needle access connector of the near-patient access port member.

2. The system of claim 1, wherein the needle access connector comprises a septum.

3. The system of claim 2, wherein the septum is external to the main branch of the near-patient access port member.

4. The system of claim 2, wherein the septum is integrated within the main branch of the near-patient access port member.

5. The system of claim 2, wherein the septum comprises an angled distal face within an interior of the main branch.

6. The system of claim 1, wherein the cannula is one of a sharp metal needle, a blunt metal needle, or a blunt plastic cannula.

7. The system of claim 1, wherein the blood draw device further comprises a distal connector interface configured to removably couple the blood draw device to the near-patient access port member.

8. The system of claim 7, wherein the distal connector interface comprises a pair of connector clips.

9. The system of claim 7, wherein the distal connector interface is configured to at least partially surround the cannula and form a safety shield around at least a portion of the cannula.

10. The system of claim 1, wherein the blood draw device further comprises a safety shield configured to surround the cannula and be selectively removable from the cannula.

11. The system of claim 1, wherein the near-patient access port member further comprises a side branch and an extension set coupled to the near-patient access port member via the side branch.

12. The system of claim 11, wherein the side branch is distally-directed relative to the main branch.

13. The system of claim 11, wherein the side branch is proximally-directed relative to the main branch.

14. A system for blood draw comprising:

a catheter adapter comprising a catheter configured to be inserted into a patient's vasculature and a side inlet defining a fluid pathway into and out of the catheter;

a near-patient access port member having a main branch comprising a distal end portion couplable to the side inlet of the catheter adapter and a proximal end portion having integrated septum therein; and a blood draw device removably couplable to the near-patient access port member, wherein the blood draw device comprises:

a cannula configured to penetrate the integrated septum of the near-patient access port member;

a flow tube configured to be advanced and retracted through the cannula; and a tube advancement tab coupled to the flow tube and configured to linearly advance and retract the flow tube through the cannula such that the flow tube is selectively directable through the blood draw device, the near-patient access port member, and the catheter adapter when the cannula of the blood draw device penetrates the integrated septum of the near-patient access port member.

15. The system of claim 14, wherein the integrated septum comprises an angled distal face within an interior of the main branch.

16. The system of claim 14, wherein the cannula is one of a sharp metal needle, a blunt metal needle, or a blunt plastic cannula.

17. The system of claim 14, wherein the blood draw device further comprises a distal connector interface configured to removably couple the blood draw device to the near-patient access port member, and wherein the distal connector interface comprises a pair of connector clips.

18. A system for blood draw comprising:

a catheter adapter comprising:

a catheter configured to be inserted into a patient's vasculature, a proximal access port having an integrated septum positioned therein, and a side inlet, wherein both the proximal access port and the side inlet define a fluid pathway into and out of the catheter;

a near-patient access port member having a main branch comprising a distal end portion couplable to the side inlet of the catheter adapter and a proximal end portion; and a blood draw device removably couplable to the proximal access port of the catheter adapter, wherein the blood draw device comprises:

a cannula configured to penetrate the integrated septum of the catheter adapter;

a flow tube configured to be advanced and retracted through the cannula; and a tube advancement tab coupled to the flow tube and configured to linearly advance and retract the flow tube through the cannula such that the flow tube is selectively directable through the blood draw device and the catheter adapter when the cannula of the blood draw device penetrates the integrated septum of the catheter adapter.

19. The system of claim 18, wherein the cannula is a blunt cannula.

20. The system of claim 18, wherein the blood draw device further comprises a distal connector interface configured to removably couple the blood draw device to the proximal access port of the catheter adapter.

* * * * *